United States Patent [19]
Pitchford et al.

[11] 3,980,568
[45] Sept. 14, 1976

[54] RADIATION DETECTION SYSTEM

[75] Inventors: Arthur H. Pitchford, Bethel Park; Robert A. Cianflone, Mount Lebanon, both of Pa.

[73] Assignee: Hankison Corporation, Canonsburg, Pa.

[22] Filed: Oct. 17, 1975

[21] Appl. No.: 623,418

[52] U.S. Cl. .............................................. 250/276
[51] Int. Cl.² .................... G01N 23/20; G21K 1/00; G21K 7/00
[58] Field of Search ............... 250/276, 394; 356/76

[56] References Cited
UNITED STATES PATENTS
3,562,525  2/1971  Constantine et al. ............... 250/394
FOREIGN PATENTS OR APPLICATIONS
1,116,865  6/1968  United Kingdom ................. 250/276

Primary Examiner—Archie R. Borchelt
Assistant Examiner—T. N. Grigsby
Attorney, Agent, or Firm—Webb, Burden, Robinson & Webb

[57] ABSTRACT

A radiation detection device comprises a radiation source and a plurality of detectors and crystals positioned thereabout to simultaneously detect certain known wavelengths. Each detector emits a signal representative of the intensity of the detected wavelength and a summing means adds the signal intensities together to give a unitary output signal. This summed output signal can then be used as a material sorter through a direct read out or can go into a function circuit which compensates an X-ray thickness gauge for changes in composition. In the latter situation, a function circuit output can be fed forward to control the machinery responsible for producing the thickness obtained.

7 Claims, 4 Drawing Figures

RADIATION DETECTION SYSTEM

BACKGROUND OF THE INVENTION

This invention relates to radiation detection devices and, more particularly, to a system which sums up the individual intensities of certain elemental constituents in a sample from a plurality of detectors and utilizes the summation as a material sorter or as an intensity input representative of density to compensate an X-ray thickness gauge for changes in composition.

Radiation detection systems have been utilized to identify elements in a sample, e.g. radiation spectroscopy, and to identify physical characteristics such as thickness, e.g. X-ray gauge.

The basic requirements for spectroscopic measurements are a radiant-energy source, a dispersion device and a detector. The source emits either all the wavelengths within a range or the wavelength which is to be measured. The dispersion element separates the radiant energy into its various components at different wavelengths and the detector measures the relative intensity of the radiant energy at those wavelengths.

A physical measurement can also be made through X-rays. For example, the process of rolling or forming metals and nonmetallic materials to a given thickness is often controlled by an X-ray thickness device which operates by passing a beam of radiation, of a predetermined wavelength, through the material with the transmitted portion of the radiation being detected by various radiation detection means. The density of the material is reflected in the amount of radiation absorbed. Therefore, calibrated thickness of material with the same chemistry permit the construction of a plot or curve from which unknown thicknesses can be determined.

The absorption coefficient of a material is a function of its composition. This is true because each element of the material has a specific atomic weight which correlates with its physical density and the density has a relationship to its absorption characteristic for a particular wavelength of radiation.

The signal from a radiation detector such as an X-ray gauge can be fed forward to cause changes in roll spacings, pressure or drive speed to maintain the desired physical thickness of the product. Should the density change, due to a change in composition, the transmitted beam will be erroneous as to a given thickness measurement.

Certain types of composition compensators for thickness measurements are known. Exemplary of these are U.S. Pat. Nos. 3,482,098; 3,210,545; and 2,988,641. It is also known that more than one element or more than one parameter can be detected at the same time through X-ray radiation techniques. Exemplary of those teachings are U.S. Pat. Nos. 3,046,399 and 3,489,901.

It is an object of our invention to obtain a signal representative of certain critical elements in a material and utilize that signal to either identify that material with respect to other similar materials and/or to compensate an X-ray thickness gauge for changes in composition in a material or from material to material.

SUMMARY OF THE INVENTION

Our invention simplifies the composition compensators employed heretofore. In addition, our invention results in a signal which can be used to sort materials and/or to compensate a thickness measurement for changes in composition. When used as a sorter, our invention is very compact and, therefore, can be portably handled to sort and identify materials. When used as a compensator, our invention provides a total count or intensity representative of certain elemental constituents and the density of the material and, therefore, a straight forward identification and correction can be made to a thickness measurement device.

Our invention is a radiation detection system in which a plurality of detectors and crystals or energy dispensive devices are positioned about a radiation source. Each detector is positioned at a particular angle for the known wavelength of an element in accordance with Bragg's Law to determine the intensity of the element based on the count of the radiated signal. The individual intensities representative of the elements which are simultaneously detected are then summed in a summing amplifier and the summation is used to identify or sort the material and/or to correct an X-ray thickness measurement for changes in composition. The correction for change in composition takes place in a function circuit which can then be fed forward to control the process equipment giving rise to the particular thickness.

DESCRIPTION OF THE PREFERRED EMBODIMENTS

Figure 1:
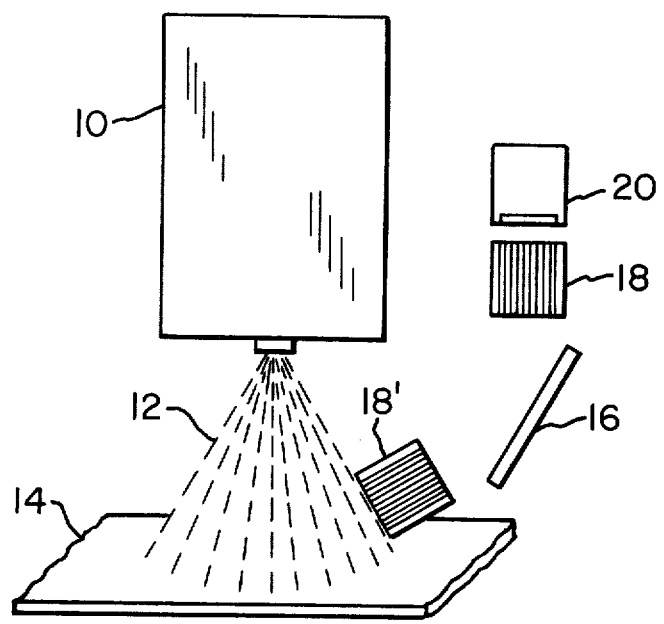
FIG. 1 is a schematic of a single channel detection system.

A standard single channel radiation detection system includes a radiation tube such as X-ray tube 10 which bombards a sample 14 with radiation particles 12, FIG. 1. The X-ray tube 10 includes the proper regulated high voltage generator, the X-ray tube filament supply and the necessary control devices. A first collimator 18', preferably of the parallel slit type, is interposed between the specimen 14 and the crystal 16. The crystal is set at the desired angle according to Bragg's Law to reflect a known wavelength of radiation. The reflected beams from the crystal 16 are characteristic of one elemental constituent of the specimen 14 and are sent through a second collimator 18 and into a detector 20. The detector 20 counts the radiation particles and a signal representing the count of the radiation particles per unit time becomes the output signal from the detector 20. Either the dispersive or the nondispersive system of detecting the characteristic radiation from each element may be used. The dispersive system utilizes the crystal grating to resolve and defract the desired spectrol line of the element into its respective radiation detector or counter. The nondispersive system utilizes a so-called pulse height analyzer or energy dispersive device to resolve the desired spectrol line of the given element.

Figure 2:
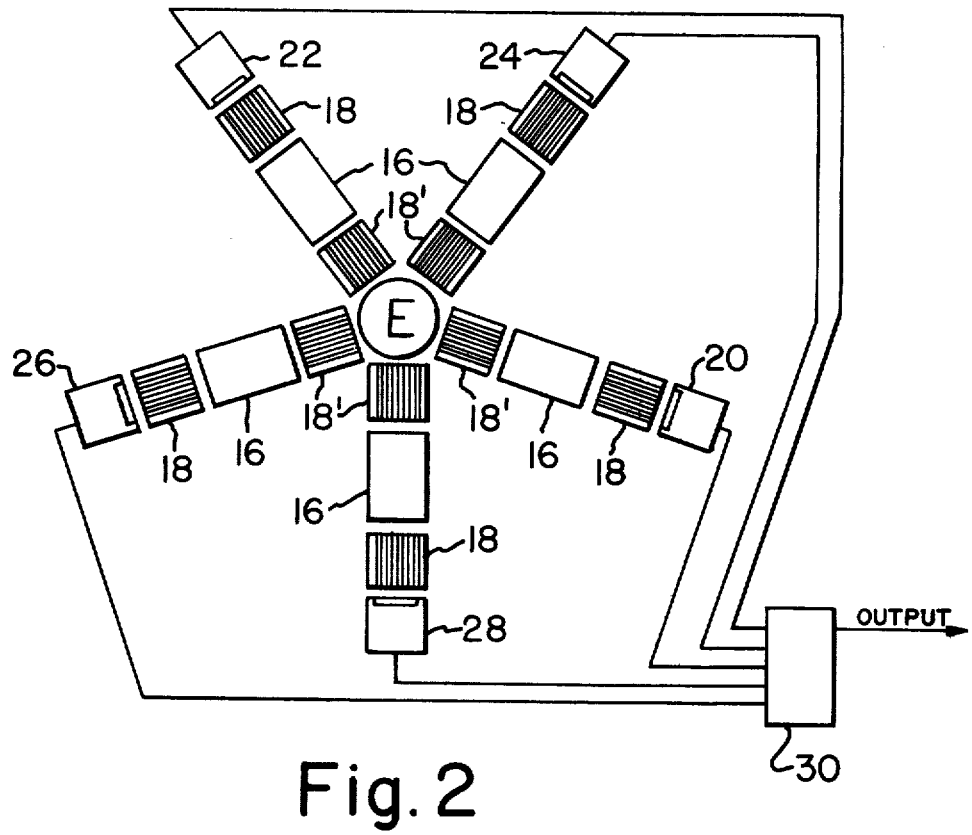
FIG. 2 is a schematic of a five channel detection system.

In our radiation detection system we provide a plurality of detectors 20, 22, 24, 26 and 28 positioned about the X-ray tube identified as E in FIG. 2. Each of the crystals 16 associated with a detector is set at a particular angle so as to reflect a wavelength of the desired elemental constituent. All of these elements in the materials are excited simultaneously and each resolved and registered simultaneously by its individual radiation detector. Collimators 18' are used between the X-ray tube E and the various crystals 16 and likewise collimators 18 are positioned between the respective cyrstals 16 and the detectors 20, 22, 24, 26 and 28. Since each crystal 16 is set at a different angle to satisfy Bragg's Law for a different elemental constituent, each detector gathers a count per unit time which is representative of the intensity of the particular element detected. This count may then be transformed into an electrical output signal.

The output signal from each respective detector 20, 22, 24, 26 and 28 is then sent to a single summing amplifier 30. The summing amplifier adds together the respective output signals, or intensities or number of counts into a single output signal representative of the total atomic weight of the elements considered and/or the density of the material. Of course, should the percentage of one constituent be so high as to produce a value or signal strength that would over shadow the intensities from the other elements present, its signal may be decreased by filtering or the signals from the other elements may be increased by amplification as is known in the art.

Figure 3:
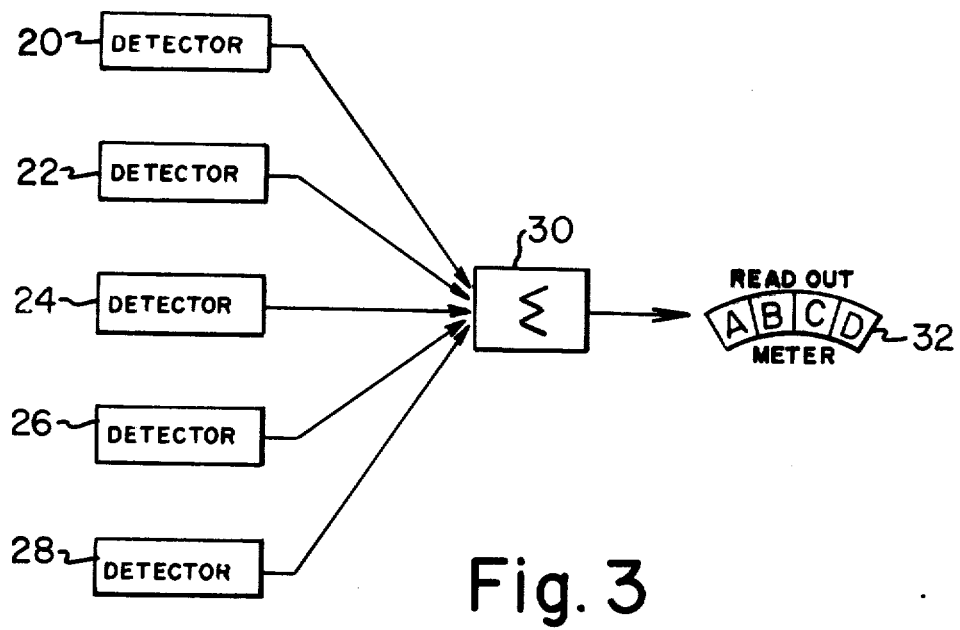
FIG. 3 is a block diagram of our invention utilized as a sorter.

The output signal from the summing amplifier 30 can go directly into a read-out meter 32, FIG. 3, for sorting materials such as metal alloys. The read-out meter 32 is illustrated as identifying four alloys A, B, C and D. Each alloy A, B, C and D has a characteristic composition represented by a range of summed output signals of the various elemental constituents in the alloy. The summed signal from summing amplifier 30 identifies which of the alloys A, B, C or D is present. As such, the system illustrated in FIG. 3 is an efficient and extremely fast way of sorting alloys and/or identifying individual alloys.

The output signal from the summing amplifier 30 can also go into a radiation thickness gauge to correct the thickness reading for changes in composition.

A typical radiation thickness gauge comprises a source of X-rays on one side of the material and an X-ray detector on the other side. The radiation which is not absorbed is transmitted through the material and the transmitted beam is compared with a predetermined value based upon measurements of a standard material of known thickness. If the thickness increases, the transmitted beam decreases thereby giving a lower reading. This reading is then compared with the standard, usually in a mini computer which forms part of the function circuit, and a correction based on a curve of the standard for different thicknesses is fed forward to the rolls to bring the thickness in line with what it should be.

Figure 4:
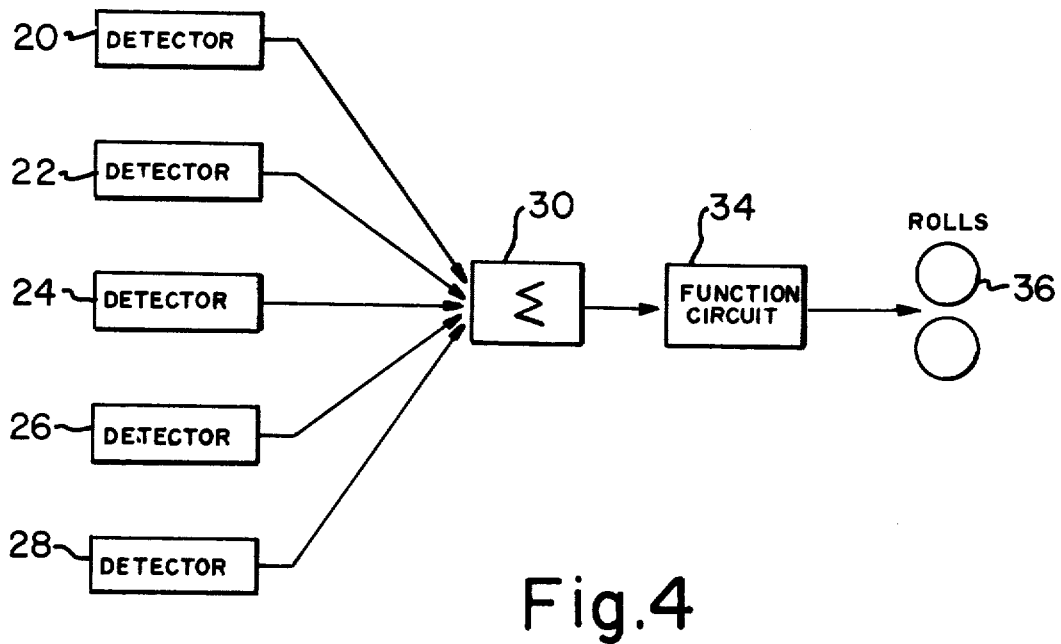
FIG. 4 is a block diagram of our invention used as composition correction for a thickness measurement.

This X-ray thickness gauge is diagrammatically illustrated as part of function circuit 34, FIG. 4. The output signal from the function circuit 34 can then be used to control the screwdown on rolls 36 so as to maintain a constant thickness of the product.

As stated, a change in composition also effects the density and thus the transmitted beam. Therefore, the summed signal from amplifier 30 is first used to identify the material as in the earlier embodiment. This identification of the material establishes the specific curve which is to be used for comparison and correction purposes to determine the signal which is fed forward to control the rolling process.

Another way in which the summed signal can be used as a correction for a thickness reading is to compare the summed output signal with a value representative of the composition of the standard material. Any difference is then converted to a signal which becomes dependent on the nominal thickness of the material. It is to be understood that the novel concept is not the correction, per se, for composition, but the utilization of the summed intensities of the elemental constituents as the input for the correction.

The crystal 16 is normally rotatable so as to permit the settings of a particular radiation detection system to be varied for different elemental constituents. The crystal may be manually rotated or can be operable through a standard goniometer which rotates the crystal at one-half the angular speed of the counter tube so that both are always in correct position to receive the various desired wavelengths emitted from the sample.

Generally, very little error is introduced by elements with atomic weights less than the matrix material. This is true since only the elements with a greater atomic weight than the matrix material have a greater density and, therefore, greater absorption characteristics. For this reason only the so-called heavier elements need be detected for identification and for correcting a thickness measurement.

The following tests reported in Table 1 were conducted on aluminum alloys of the 1100, 3003 and 5052 type. The crystal employed was a lithium fluoride 200 crystal and the X-ray tube was operated at a voltage of 30 kv.

TABLE I

*Aluminum Alloy Analysis
Radiation Particle Count In 30 Seconds

| Alloy | Fe | Cr | Mn | Cu | Zn | Ti | Total |
|-------|-------|------|-------|------|------|-----|-------|
| 1100  | 14504 | 494  | 1160  | 2941 | 1272 | 348 | 20719 |
| 3003  | 14454 | 528  | 20817 | 3274 | 1830 | 500 | 41403 |
| 5052  | 7086  | 3628 | 1395  | 1270 | 1459 | 347 | 15186 |

*Each result is average of five different samples of same thickness.

The total count for each alloy type illustrates the wide variation in density factors attributable to compositions of a sample of the same thickness. The total count in Table 1 could then be utilized directly as an alloy sorter, FIG. 3, wherein the read out would merely be an identification of whether the product was an 1100, 3003 or 5052 aluminum alloy. In addition to or alternatively, the total count could be used in a system such as that illustrated in FIG. 4 wherein the total count could be used to compensate the X-ray thickness gauge utilized during the rolling of these different alloys.

We claim:
1. A radiation detection device comprising:
   A. a radiation source for emitting radiation particles onto a sample;
   B. a plurality of crystals, each positioned about the radiation source to simultaneously receive reflected radiation particles from the sample and reflect a given wavelength from an elemental constituent of the sample;
   C. a plurality of radiation detectors, each positioned with respect to a crystal to simultaneously detect the given wavelength;
   D. summing means for receiving signals representative of each of said detected wavelengths from said detectors and for summing said signals into an output signal; and

E. identifying means for receiving said output signal from the summing means and utilizing said summed signal to identify a compositional characteristic of the sample.

2. The detecting device of claim 1 wherein said identifying means comprises a product sorter having stored data on a plurality of compositional characteristics for different materials so that the summed signal is compared thereagainst to identify the material.

3. The detecting device of claim 1 wherein the identifying means is associated with a function circuit for transmitting the summed signal as an output signal representative of the density of the sample.

4. The detecting device of claim 3 including an X-ray thickness gauge associated with the function circuit for receiving said density output signal from the function circuit and compensating the X-ray thickness gauge for changes in sample density resulting from changes in sample composition.

5. The detecting system of claim 4 including a feed forward system for receiving a compensated thickness signal and directing the signal to control a process giving rise to the sample thickness.

6. A process for identifying a compositional characteristic of a sample comprising:

A. subjecting the sample to a radiation detecting device comprising a radiation source, a plurality of crystals each set to reflect a given wavelength of an elemental constituent of the sample and a plurality of detectors, each positioned with respect to a crystal to detect the given wavelength;

B. bombarding the sample with radiation particles;

C. simultaneously reflecting the particles off each of the crystals;

D. simultaneously counting the reflected particles in each of the detectors;

E. simultaneously transforming the counted particles into an output signal;

F. simultaneously transmitting the output signal to a summing means;

G. summing the individual output signals into a single output signal characteristic of the composition of the sample; and H. utilizing the single output signal to identify the sample.

7. The process of claim 6 including the step of compensating an X-ray thickness gauge for changes in composition through use of the sample identifying output signal.

* * * * *